(12) United States Patent
Gajdos et al.

(10) Patent No.: US 11,497,478 B2
(45) Date of Patent: Nov. 15, 2022

(54) TUNED MEDICAL ULTRASOUND IMAGING

(71) Applicant: Siemens Medical Solutions USA, Inc., Malvern, PA (US)

(72) Inventors: Miroslav Gajdos, Kosice (SK); Bimba Rao, San Jose, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 397 days.

(21) Appl. No.: 15/984,502

(22) Filed: May 21, 2018

(65) Prior Publication Data

US 2019/0350564 A1  Nov. 21, 2019

(51) Int. Cl.
*A61B 8/00* (2006.01)
*A61B 8/08* (2006.01)
(Continued)

(52) U.S. Cl.
CPC .............. *A61B 8/585* (2013.01); *A61B 8/463* (2013.01); *A61B 8/5292* (2013.01); *G06N 3/08* (2013.01); *G06T 5/00* (2013.01); *G06N 3/04* (2013.01); *G06T 2207/10132* (2013.01); *G06T 2207/20081* (2013.01); *G06T 2207/20084* (2013.01); *G06T 2207/30004* (2013.01); *G16H 30/20* (2018.01)

(58) Field of Classification Search
CPC ....... A61B 8/585; A61B 8/5292; A61B 8/463; A61B 8/5215; A61B 8/565; A61B 8/54; G06T 5/00; G06T 2207/20081; G06T 2207/20084; G06T 2207/30004; G06T 2207/10132; G06N 3/08; G06N 3/04; G06N 20/00; G16H 30/20; G16H 40/40; G16H 50/20; G09B 23/286; G09B 19/00
See application file for complete search history.

(56) References Cited

U.S. PATENT DOCUMENTS 6,656,120 B2   12/2003   Lee et al.
7,295,706 B2   11/2007   Wentland et al.
(Continued)

FOREIGN PATENT DOCUMENTS

JP   2018505705        3/2018
KR   20170032238       3/2017
KR   1020170098481 A1  8/2017

OTHER PUBLICATIONS

Butterfly "A New Startup Wants to Put Ultrasound Technology in Every Home" https://www.butterflynetwork.com/. Accessed May 15, 2018.

*Primary Examiner* — Joseph M Santos Rodriguez
*Assistant Examiner* — Kaitlyn E Sebastian

(57) ABSTRACT

Machine learning trains to tune settings. For training, the user interactions with the image parameters (i.e., settings) as part of ongoing examination of patients are used to establish the ground truth positive and negative examples of settings instead of relying on an expert review of collected samples. Patient information, location information, and/or user information may also be included in the training data so that the network is trained to provide settings for different situations based on the included information. During application, the patient is imaged. The initial or subsequent image is input with other information (e.g., patient, user, and/or location information) to the machine-trained network to output settings to be used for improved imaging in the situation.

10 Claims, 4 Drawing Sheets

(51) Int. Cl.
  *G06T 5/00*  (2006.01)
  *G06N 3/08*  (2006.01)
  *G16H 30/20*  (2018.01)
  *G06N 3/04*  (2006.01)

(56) References Cited

U.S. PATENT DOCUMENTS

| | | |
|---|---|---|
| 7,648,460 B2 | 1/2010 | Simopoulos et al. |
| 7,680,312 B2 | 3/2010 | Jolly et al. |
| 7,747,054 B2 | 6/2010 | Zhou et al. |
| 7,876,934 B2 | 1/2011 | Georgescu et al. |
| 8,885,926 B2 | 11/2014 | Seung et al. |
| 9,536,054 B1 * | 1/2017 | Podilchuk ............ G06T 7/0012 |
| 10,726,546 B2 * | 7/2020 | Mihalef ................ A61B 8/06 |
| 2003/0097065 A1 | 5/2003 | Lee et al. |
| 2003/0114753 A1 * | 6/2003 | Sharma ................ G01S 15/899 600/437 |
| 2005/0010098 A1 | 1/2005 | Frigstad et al. |
| 2006/0064017 A1 | 3/2006 | Krishnan et al. |
| 2006/0241455 A1 | 10/2006 | Shvarts |
| 2012/0148156 A1 | 6/2012 | Sehnert |
| 2014/0221832 A1 * | 8/2014 | El-Zehiry ............ G16H 40/63 600/437 |
| 2015/0238148 A1 * | 8/2015 | Georgescu .......... G06K 9/4628 600/408 |
| 2016/0350620 A1 * | 12/2016 | Rao ...................... G06T 5/001 |
| 2018/0144214 A1 * | 5/2018 | Hsieh .................. G06K 9/036 |
| 2019/0213474 A1 * | 7/2019 | Lin ...................... G06K 9/6256 |
| 2019/0333210 A1 * | 10/2019 | Mihalef ................ A61B 8/06 |
| 2020/0065656 A1 * | 2/2020 | Song ..................... G06N 3/08 |

* cited by examiner

TUNED MEDICAL ULTRASOUND IMAGING

BACKGROUND

The present embodiments relate to medical ultrasound imaging. An increasing and aging patient population is creating a demand for improved healthcare efficiency. This has led to a desire for ultrasound imaging workflow improvement from the standpoint of increased patient throughput, reducing examination times and user stress through repetitive motion, and better standardization of examinations. Part of the ultrasound workflow is tuning the imaging parameters to get to the best image suited for diagnosis of each patient. The tuning to find this image is a time consuming and challenging task.

It is difficult to find a "one size fits all" system setting that can produce satisfactory diagnostic images across different patient types, anatomies, and pathologies. It is also difficult to find one setting that meets different user preferences across various global regions. A user having to tune the settings for every patient examination leads to increased examination time, inefficient workflow, operator fatigue and even reduced diagnostic confidence.

In current day products, the problem is addressed by creating presets in the factory for different patient types and applications. These factory presets work to a certain extent but cannot cover the large variety of patient types and do not address user preferences. There are some knowledge-based techniques that use artificial intelligence or other techniques to segment the image. The segmentation maybe then be used to set the imaging system parameters such as frequency, focus, or depth, but the segmentation is focused on the anatomy. This approach requires an expert review to create training data and does not address other patient variability nor user preferences.

SUMMARY

By way of introduction, the preferred embodiments described below include methods, systems, instructions, and computer readable media for machine learning to tune settings and imaging optimization using a machine-learned network. For training, the user interactions with the image parameters (i.e., settings) as part of ongoing examination of patients are used to establish the ground truth positive and negative examples of settings instead of relying on an expert review of collected samples. Patient information, location information, and/or user information may also be included in the training data so that the network is trained to provide settings for different situations based on the included information. During application, the patient is imaged. The initial or subsequent image is input with other information (e.g., patient, user, and/or location information) to the machine-trained network to output settings to be used for improved imaging in the situation.

In a first aspect, a method is provided for machine learning image optimization with a medical ultrasound scanner. The medical ultrasound scanner images a patient where the imaging provides a first image where one or more settings are changed after display of the first image and provides a second image resulting from the change in the one or more settings. A machine trains a first neural network to output a setting value based on an input image and patient information. The training includes the first and second images as negative and positive examples, respectively, in the training data. The first neural network as trained is stored.

In a second aspect, a method is provided for image optimization with a medical ultrasound scanner. A medical ultrasound scanner images a patient using first settings. A first image from the imaging using the first settings and patient information for the patient are input to a machine-learned network. The machine-learned network outputs second settings in response to the inputting of the first image and the patient information. The medical ultrasound scanner re-images the patient using the second settings. A second image from the re-imaging is displayed.

In a third aspect, a system is provided for tuned ultrasound imaging. An ultrasound scanner is configurable based on first and second values of imaging parameters. A processor is configured to determine the second values of the imaging parameters with a machine-trained network in response to input of a first image of a patient, the first values of the imaging parameters used for the first image, and patient information for the patient. A display is configured to display a second image of the patient generated by the ultrasound scanner configured by the second values.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Patient-specific ultrasound image optimization is provided. Artificial intelligence (AI)-based algorithms enable an ultrasound scanner to "learn from experience" by analyzing data produced as part of patient imaging to determine ground truth. The capabilities of AI are used to automate tuning of imaging parameters and so improve ultrasound imaging workflow. The tuning may be specific to the patient situation, location of imaging, and/or user by applying patient information, location, and/or prior user selection with the trained AI. Imaging parameters are automatically tuned for different patients, anatomies, user preferences, regional preferences, types of view, and/or pathologies situations to provide an ultrasound image suited for diagnosis. Imaging may be customized to every patient as well as user, leading to significant increase in diagnostic confidence and customer satisfaction. Examination time may be reduced, and patient throughput may be increased.

To gather the training data, low and high-quality images and corresponding settings are derived from the user workflows in examining patients. There is no need to manually label the images by an expert, as is the case with most supervised learning AI algorithms. This may result in savings in development time and effort.

Artificial neural networks (ANN) are used in function approximation and classification tasks, including image classification and segmentation. An ANN or other machine learning setup may be used for automated imaging parameter tuning. For ultrasound machines, there is demand for high patient throughput and high ultrasound image quality. The capabilities of ANN to automate tuning of imaging parameters may result in good quality ultrasound images without the need for or with less user manipulation. With this approach, the examination time might be decreased as the clinical user spends less time manually tuning imaging parameters to get an ultrasound image suited for diagnosis.

Figure 1:
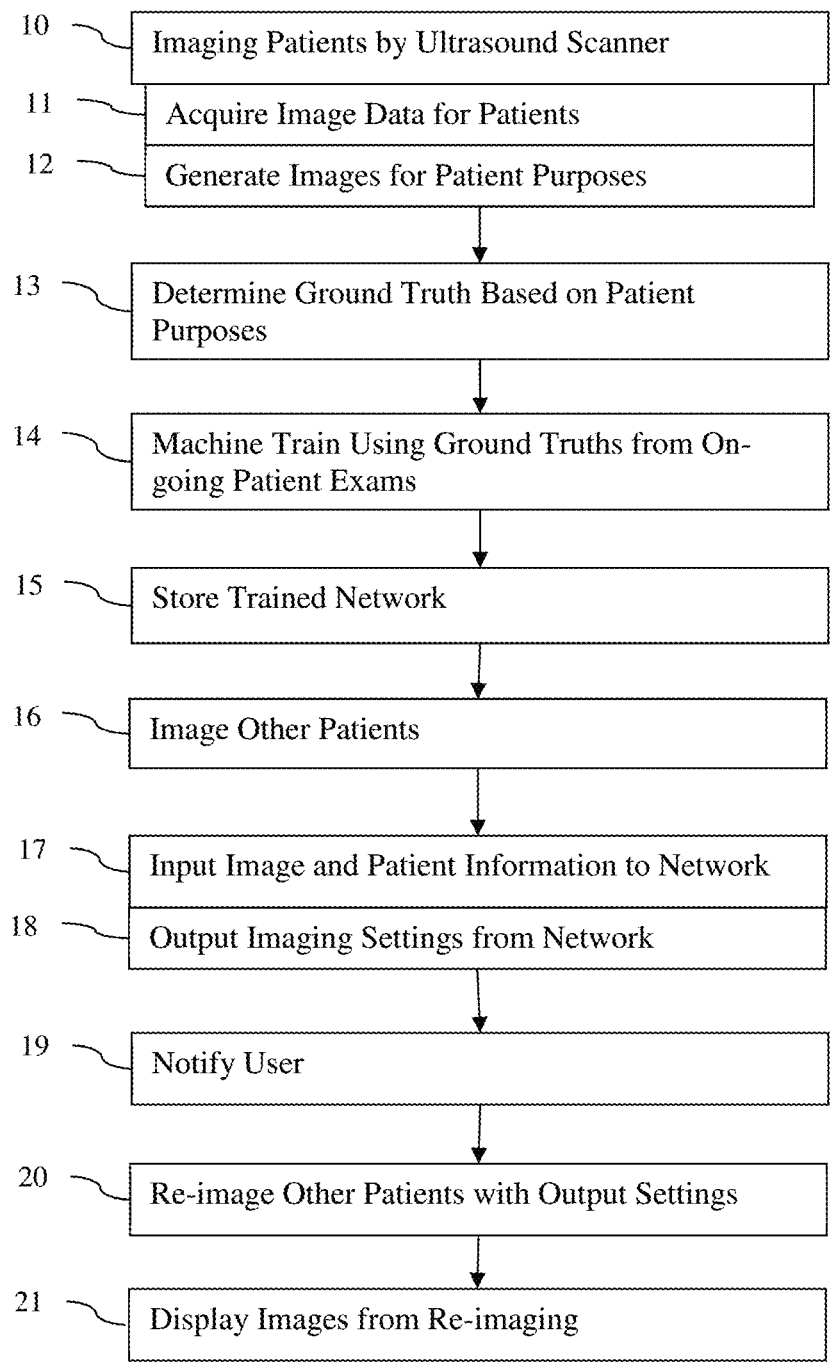
FIG. 1 is a flow chart diagram of one embodiment of a method for machine learning to tune and application of a machine-learned network to tune in medical ultrasound imaging.

FIG. 1 shows one embodiment of a method for machine learning image optimization and/or image optimization with a medical ultrasound scanner. Acts 10-15 correspond to collecting training data and machine training a network to output imaging parameter settings. Acts 16-21 correspond to use of the trained network to output imaging parameter settings for imaging a patient. The method may be just the training portion or just the application in other embodiments.

For gathering training data, one or more users of the medical ultrasound scanner interact with the imager or the medical record of the patient for examining a patient. During an examination workflow, various images are generated in sequence where the user discards some images and alters the settings to provide an image captured for diagnosis. These low and high-quality images are derived from the user workflow, so there is no need to manually label them. This interaction for treatment, diagnosis, and/or prognosis of the patient indicates a ground truth (e.g., settings for positive (captured) or negative (discarded)) for a sample that is the image, patient information, location information, and/or user information. This ground truth is used to train or retrain a machine-learned network to be applied by the medical scanner or other scanner for examination of other patients. The machine learning is used to optimize and personalize the system to a specific patient type, anatomy type, view type, user preference, and/or regional preference.

Figure 5:
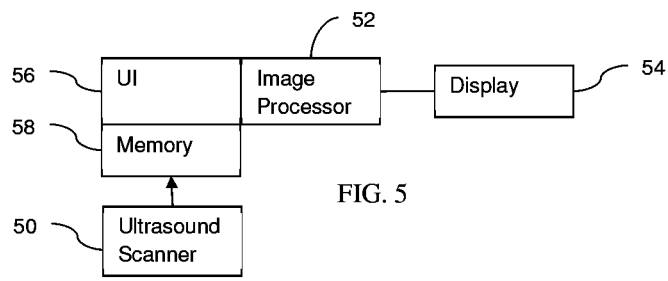
FIG. 5 is a block diagram of one embodiment of a system for tuned ultrasound imaging.

The method of FIG. 1 is implemented by a medical imaging system, such as a medical ultrasound scanner. In one embodiment, the system of FIG. 5 implements the method of FIG. 1. For example, one or more medical ultrasound scanners perform the imaging of acts 10, 16, and 20. The medical scanner, workstation, or other processor determines the ground truth based on data created for patient purposes in act 13, machine trains in act 14, and/or stores, with a memory, in act 15. The same or a different ultrasound scanner, workstation, and/or processor uses the trained network in act 17, outputs settings in act 18, and notifies in act 19. A user input device and display, interacting as a user interface controlled by the scanner, workstation, and/or processor, handles any adjustment to settings, authorization of network-proposed settings, and/or imaging control. A display device displays the images resulting from the imaging acts, such as performing act 21. Other devices may perform or be used in the performance of any of the acts.

Other types of medical scanners than ultrasound may be used, such as computed tomography, x-ray, or magnetic resonance.

The acts are performed in the order shown (top to bottom or numerical) or another order. Additional, different, or fewer acts may be provided. For example, acts 16-21 are not provided. As another example, acts 10-15 are not provided. In other examples, acts for gathering or inputting location, patient, and/or user information are provided.

In act 10, the medical ultrasound scanner images patients. Any medical diagnostic and/or therapeutic ultrasound imager may be used. Beamformers and a transducer generate acoustic energy and receive echoes to scan the patient. A detector, filter, scan converter, and/or other devices in an image processor generate an image from the scan data. Acts 11 and 12 are one example of the imaging of a patient.

The medical scanner scans different patients. For each patient, the scan is for prognosis, diagnosis, and/or treatment of the patient. The patient is being scanned to help the patient. A treating physician (e.g., user) orders the scan, a technician (e.g., user) performs the scan, and a radiologist (e.g., user) may review results of the scan. These users of the scanning are helping the patient, so the data is for patient purposes.

In act 11, the medical scanner images by scanning. Energy is transmitted to the patient, and the response is measured. The patient is scanned at a point, along a line, over an area or plane, and/or in three dimensions. Any part of the patient may be scanned.

The medical scanner acquires image data representing the patient. The medical scanner provides medical data representing a region of the patient. The medical scanner may directly provide the image data, such as providing in an image processing pipeline of the medical scanner. The medical scanner may indirectly provide the image data, such as routing the image data through a memory or computer network. The image data may be accessed from a picture archiving and communications system (PACS) server or electronic medical record.

In act 12, the medical scanner generates one or more images of the patient from the image data. The measured signals from the patient are processed to generate an image. The image is scalar values that may be formatted and/or mapped to display values or is display values (e.g., RGB). Any image processing may be used, such as filtering, reconstruction, rendering, segmentation, and/or landmark detection. The image may include graphics, such as wireframes or outlines for detected landmarks or segmented objects.

For act 10, the medical scanner is configured for acquiring the image data and generating the image form the image data. Values for various scan and/or post-processing settings are set. The values or settings of various imaging parameters may control transmission, reception, or post-reception processing (e.g., filtering, detecting, and/or reconstruction). Example scan settings include transmit frequency, receive frequency, scan line format, scan line density, pulse repetition frequency, overall gain, depth gain, dynamic range, focal depth, scan depth, focal position, filter kernel, spatial filter parameters, temporal filter parameters, noise thresholds, motion thresholds, color mapping, three-dimensional rendering parameters, and/or other scan or post-scan settings for generating an image. In one embodiment, a machine-learned network is used for acquiring the image data. For example, the machine-learned network was trained to output scan settings to use based on patient-specific input data.

Application of the machine-learned network to patient data provides values for the scan parameters.

The imaging generates data. A log of the performance of the medical scanner for the scan, image data, an image, scan settings, and/or other data is generated by the medical scanner for the examination of the patient. Other data may be accessed or used for the examination, such as lab results, patient medical history, patient clinical data, data from a pressure and/or heart monitor (e.g., ECG), and/or other data. This patient data is gathered for the patients being treated or diagnosed by the medical facility and professionals.

Other data may be obtained. For example, a location (e.g., region designation) is provided for the scanner and/or patient. As another example, a user identification is obtained. The user identification may be used to obtain additional user information, such as age, gender, role (e.g., technician, radiologist, or treating physician), vision information (e.g., color blind and/or visual acuity), and/or image preferences.

In act 13, a processor determines a ground truth for an image or images generated for the patient. The ground truth is determined by the medical scanner, a workstation, server, or other computer.

Various data sources may be used to determine the ground truth, such as an image of the medical scanner, an image or scan settings from a PACS database, scanner log data in the medical scanner or a maintenance database, electronic medical record for the patient, data from other sensors, and/or other data. In one embodiment, the medical scanner tracks generated images, settings for the images, and whether the image is captured or results in rescanning. The data may be stored local to the medical scanner and/or remotely from the medical scanner.

The data is generated for the patient by the users of the medical scanner. The treating physician, nurses, scanning technician, radiologist, and/or other medical professional providing medical services to the patient generate the data. The ground truth is determined from the data created for patient purposes. For example, an image generated for patient examination is captured for storage or analysis for the patient, indicating acceptance of the image. The image and corresponding data for the patient examination indicate the ground truth. The ground-truth is inferred from the downstream events that the patient and/or the medical image encounters during the day-to-day clinical practice. There is not a dedicated process whereby the ground-truth is created for training an algorithm. Rather, the ground-truth is created by the virtue of having access to other contextual data from the clinicians, IT systems, etc. for the patient. The ground truth is an acceptance of an image, a rejection of the image, a final image after any changes, or other indication of use of the data for the patient (e.g., the end result from examination of the patient).

In one embodiment, the indication of acceptance or change of an image for the patient may provide positive or negative ground truth for that image and corresponding settings in the imaging situation (e.g., given patient, user, and/or location information). The image after change may provide a positive ground truth. The acceptance may be indicated by storage or capture of the image in the patient medical record, such as transfer of the image to PACS, log data indicating the image as the final or last image, or other indication of acceptance or not. For example, the log data may indicate repetition of the same scan or regeneration of the image from the same image data with one or more different settings. If within a threshold time and/or based on saving or transfer, the acceptance or rejection may be indicated.

Often several scans are repeated due to poor quality. There could be several reasons for the poor quality—operator error, motion artifact due to breathing and/or patient movement, incorrect contrast timing, etc. The medical scanner may automatically detect the poor-quality scan and use the poor-quality image as a negative example in the ground-truth training database. The poor quality is indicated by rescanning, failure to save the image in the patient's medical record, overwriting of the image, log data, and/or a measure of image quality. For example, the repeat scan may be identified when an operator performs the exact same scan in succession within a threshold time. In such a case, the medical scanner assumes that the first scan was of poor quality (ground-truth label), while the next scan is of diagnostic quality (ground-truth label). In another example, the repeated imaging is detected by the scanner by analyzing the usage log files that are produced by the scanner.

The workflow for imaging of the patient determines the ground truth. Where one or more settings are changed after display of an image, the image and corresponding settings are a negative ground truth. For a typical workflow, the initial image of the patient generated after positioning the field of view over the patient region of interest is based on default settings. User input settings may be used for the initial or other image resulting in a poor-quality image. Failure to capture the image in the patient's medical record indicates a negative ground truth. In response to a poor-quality image, the user alters one or more settings to improve the imaging. Where the change to the settings results in capture of the image for the patient, this later image and corresponding settings are a positive ground truth.

Figure 2:
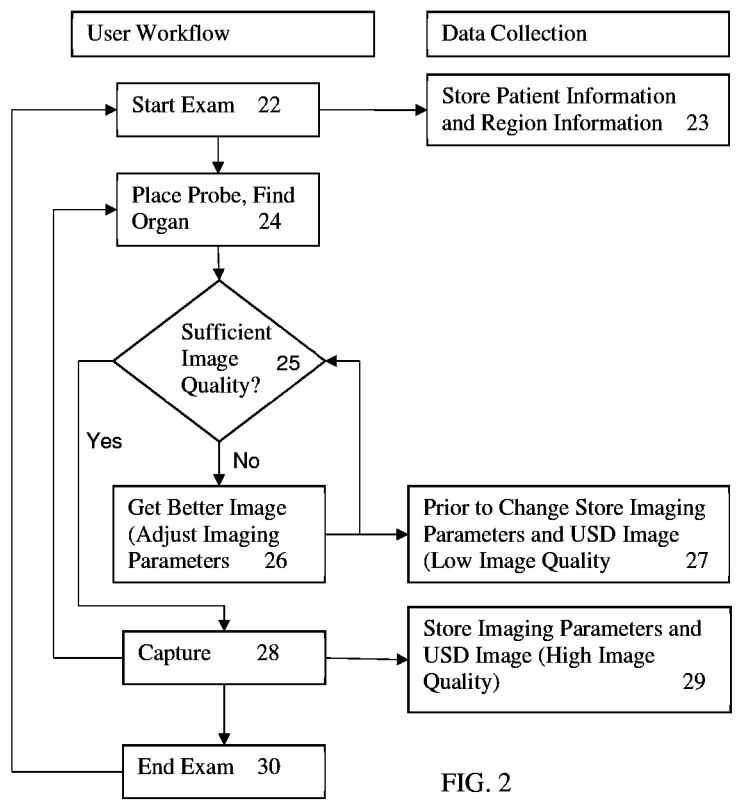
FIG. 2 illustrates an example workflow for collecting training data from on-going patient examination.

FIG. 2 shows an example workflow for examining a patient and for training data collection based on the patient-focused examination. The inputs and outputs are derived from the user workflow as opposed to conventional methods where the "labeling" is done manually as part of a review of a collection of samples.

In act 22, the examination is started by the user using the medical ultrasound scanner. The scanner is configured by the user to scan the patient, such as selecting a set of default settings based on the examination to be performed. The user may input or override one or more settings.

In act 23, the start of the examination in act 22 triggers collection or storage of patient, user, and/or region information. The patient information is input to the scanner and/or accessed from an electronic medical record of the patient. Example patient information includes height, weight, age, gender, body mass index, prior history, genetic information, laboratory results, and/or measures of patient function (e.g., heart rate, temperature, or pressure). The location and user information may be input, solicited from the user, and/or accessed from a database.

In act 24, the transducer probe is positioned on the patient and moved to generate an image of the region of interest in the patient. For example, the region of interest is a given organ, so the probe is moved relative to the patient to image the organ with the current settings.

In act 25, the user determines whether the resulting image has sufficient quality. For example, an image of the heart may not show the desired chamber or chambers with sufficient contrast and/or resolution. Where the image is not sufficient, the user changes one or more settings to generate a better image in act 26. Based on this change, the poor quality image and corresponding settings are stored or collected in act 27 as a negative example. Where the image may be diagnostically useful, the user captures the image in act 28. By depressing a capture button, the image is recorded for later use to diagnose the patient. The captured image and the corresponding settings are stored or gathered in act 29 as a positive example. The process may be repeated to capture any number of images of the same or different views of the region of the patient. The examination ends in act 30 after capturing all of the desired images.

In an example, the settings are represented by an index N starting with 0 for an initial image (IMG). Where the imaging parameters (IP) are updated from 0 to 1 without capture of IMG0, IP0 and IMG0 are stored in act 27 as a negative example. Where the IP are updated from 1 to 2 without capture of IMG1, IP1 and IMG1 are stored in act 27 as another negative example. Where the IMG2 is captured in act 28, IP2 and IMG2 are stored in act 29 as a positive example. Where the imaging parameters (IP) are updated from 2 to 3 without capture of IMG3, IP3 and IMG3 are stored in act 27 as a negative example. Where the IP are updated from 3 to 4 without capture of IMG4, IP4 and IMG4 are stored in act 27 as another negative example. Where the IP are updated from 4 to 5 with capture of IMG5, IMG5 and IP5 are stored in act 29 as a positive example. The training dataset includes: inputs of patient info, region info, IP0, IMG0 and an output of IP2 as desired; inputs of patient info, region info, IP1, IMG1 and an output of IP2 as desired; inputs of patient info, region info, IP2, IMG2 and an output of IP2 as desired; inputs of patient info, region info, IP3, IMG3 and an output of IP5 as desired; inputs of patient info, region info, IP4, IMG4 and an output of IP5 as desired; and inputs of patient info, region info, IP5, IMG5, and an output of IP5 as desired. In alternative embodiments, the settings from any previous image leading to the stored image are used (e.g., store IP2 for IMG3). IMG0, IMG1, IMG3, and IMG4 are images which need tuning due to low image quality, and IMG2 and IMG5 are images of high or sufficient image quality, which do not need tuning.

Many datasets are collected from real examinations done by one or more ultrasound scanners. The machine software (SW) collects the data without interruption to the user as the examination is performed. The data of interest is the ultrasound images which the clinical user starts to tune (images with insufficient quality), ultrasound images with which the clinical user is satisfied (image with sufficient quality, this is the one captured during image store), and the imaging parameters values for the low quality and the high-quality images.

By collecting other information (e.g., user, patient, and/or location), the various datasets may be associated with different imaging situations. The settings and corresponding image quality may vary by patient condition, pathology, anatomy, location (i.e., region), and/or user preference. By collecting the images, image settings, and other information, the training data may include information from which variance by situation may be determined using maching training.

The collected training data and determined ground truth or information that may be used to automatically determine the ground truth are provided to a machine for machine training. The datasets may be stored on local storage (e.g., hard disk drive) and collected manually during ultrasound machine maintenance, service or by demand. The datasets may be uploaded to a third-party storage (e.g., scanner manufacturer storage) via a web/cloud service. The dataset may be stored as part of DICOM as private tag, so that, when DICOM is exported to PACS, the PACS is queried for the datasets. Other approaches for the collection of the datasets from one or more ultrasound scanners may be used.

Returning to FIG. 1, a machine performs machine training using the collected datasets in act 14. The machine is a processor of the medical scanner, a server, a workstation, or a computer. Based on the training data (e.g., examples and ground truth), the artificial intelligence system is trained to produce the desired output from unseen input data. The artificial intelligence or intelligence is machine trained to output values of image parameters (i.e., imaging settings) given an input. A machine, such as an image processor, computer, server, or other device, learns from the samples to provide an output. Using machine-learning, complex relationships between large numbers (e.g., tens, hundreds, thousands, or more) of input variables to any number of output variables are extracted from the large number of samples based on the ground truth.

The training is for imaging in any context. One model may be learned for any number of imaging situations. Alternatively, different models are trained for different situations. The different situations may include different ultrasound scan modalities (e.g., different model for B-mode, Doppler Tissue, flow mode, M-mode, and/or spectral Doppler mode). The different situations may include different types of tissue of interest (e.g., liver versus kidney), and/or different diagnostic purpose or workflow (e.g., cancerous lesion versus bone calcification). The collected dataset maybe be clustered into groups. Based on the groups, multiple models might be created (e.g., models per probe type, patient type, exam type, or models per region).

Any now known or later developed machine learning may be used. Regression, classification, and/or reinforcement learning are used. Regression training learns a range or continuous output by minimization of a metric. Classification learns disparate outputs. Reinforcement learning learns a sequence of actions with feedback. Neural network, Bayes network, probabilistic boosting tree, or support vector machine training may be used. Hierarchal, cascade, or other approaches may be used. Supervised, unsupervised, or semi-supervised machine learning may be used.

To train, features are extracted from the input data. Haar wavelet, steerable, gradient, or other features may be extracted from image data or images. Alternatively, the input data itself (e.g., pixel or color values of the rendered image) is used and the learning determines features, such as with deep learning. In deep learning, the training learns convolution kernels, weights, and/or connections from the input images to generate the output. Deep learning models high-level abstractions in data by using multiple processing layers with structures composed of multiple non-linear transformations, where the input data features are not engineered explicitly. The deep learning provides the features used by other machine training to learn to output. Deep learned, sparse auto-encoding models may be trained and applied. The machine training is unsupervised in learning the features to use and how to classify given an input sample (i.e., feature vector).

Figure 3:
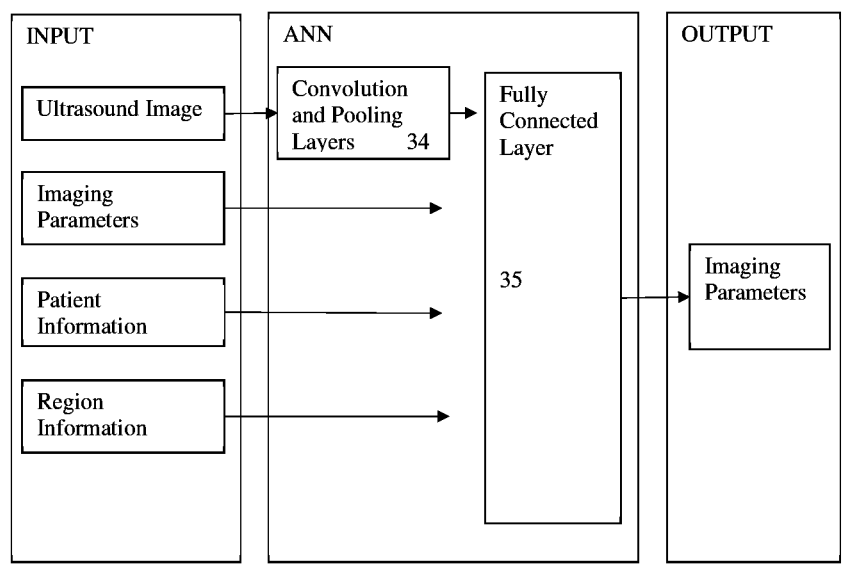
FIG. 3 illustrates an example machine learning network architecture.

Any artificial neural network architecture for the deep learning may be used. The neural network architecture defines the neural network used to train and the resulting trained or machine-learned model. The neural network is trained to output one or more setting values based on an input image with or without other input information (e.g., patient, location, and/or user information). In one embodiment, the network is a deep convolutional neural network, which may match or exceed human performance. FIG. 3 shows an example network architecture. The training data is represented by the collected input. In this example, the collected input is the images, settings for the images, patient information, and location (i.e., region) information. The ground truth is also provided by the labels for the settings, such as positive and negative labels for the different settings. The neural network architecture includes any number of convolution and pooling layers 34, which are responsible for extracting image features from ultrasound images. The neural network architecture also includes a fully connected layer, which is responsible for function approximations and/or classifications from the output of the layers 34 and the collected information. In other embodiments, some or all the other information is input to the convolution and pooling layers 34. Other architectures may be used. The layers 34 and 35 may be trained together or separately. For example, the convolution and pooling layers 34 are from an existing network (e.g., Alexnet), and are used for training the fully connected layer 35.

The training is based on the ground truth and the corresponding data, such as the image, settings, and/or other information. The ground truth identified from the examination of the patient and the data from the examination of the patient are used in the training. Many samples of the same type of data are input. To learn statistical or other relationships that may be sufficiently complex that a human cannot perceive the relationships in a same level, tens, hundreds, or thousands of samples are provided. Re-training may occur upon acquiring additional samples and ground truth for examinations of patients.

For training, the goal or ground truth information is input. The artificial intelligence system is trained with labeled data (e.g., input images with settings). When a meaningful number of datasets is available, the neural network is trained from the collected datasets. For example, the collected datasets are (1) inputs of ultrasound images of low quality, imaging parameter settings for the images of low quality, patient information, region information and user information with ground truth output of an associated or final imaging parameter settings of high quality and (2) inputs of ultrasound images of high quality, imaging parameter settings for the images of high quality, patient information, region information and user information with ground truth output of the associated imaging parameters of the images of the high quality. In other embodiments, negative examples are used as the inputs where the ground truth output is the parameter settings of the images with low quality while also using positive examples with the ground truth output being the settings of the images with high quality. The training learns the settings that distinguish from low and high quality based on the negative and positive samples and other information.

The settings for sufficient quality imaging may be different for different patients, even for a same mode of imaging, pathology being diagnosed, and/or anatomy being imaged. The patient information is used in the machine training to learn to provide settings for different patient situations. Clinical characteristics of the patient (e.g., height, weight, age, gender, and/or BMI), patient history, and/or laboratory results are provided for the different samples of the training data.

The settings for sufficient quality imaging may be different for different locations. The location information is used in the machine training to learn to provide settings for different regions, such as by county, state, and/or country. Different regions may have different demands, desires, or expectations for image sufficiency. The training data includes regional locations for the medical ultrasound scanner or examinations for the samples.

The settings for sufficient quality imaging may be different for different users, even for a same mode of imaging, pathology being diagnosed, and/or anatomy being imaged. The user information is used in the machine training to learn to provide settings for different user situations. The age, gender, role, or other characteristic of the user may result in different versions of sufficient images. The machine training may provide for user-specific settings so the user-specific preferences for imaging are considered in tuning the imaging parameters.

In act 15, the trained artificial intelligence is stored. The trained model is stored in a memory. Any memory may be used. The memory used for the training data may be used. For application, the memory may be in another device. For example, the trained model is stored in a memory of a medical ultrasound scanner or workstation. A server implementing one copy of the trained model may be used for different patients. Multiple copies of the trained model may be provided to different physicians, medical ultrasound scanners, and/or workstations for use by different physicians for different patients.

The stored machine-learned network is used to optimize imaging by a medical ultrasound scanner in acts 16-21. The settings to image are tuned using the machine-learned network. For example, the trained ANN is deployed in the ultrasound machine. By using the settings output from the network, a diagnostically useful image is more likely obtained for any given patient. The examination time for the patient may be reduced, increasing patient throughput for the ultrasound scanner.

In act 16, a medical ultrasound scanner images a patient using settings. The scanner is one of the scanners used to collect the training data or a different scanner. The patient is one of the previous patients used for collecting training data (e.g., a follow-up examination) or a different patient. The scanner is operated by a same user involved in collecting the training data or a different user.

The medical scanner images the patient. The imaging is performed as discussed for acts 10-12. The imaging is performed for diagnosis, prognosis, and/or treatment of the patient. The imaging is performed for any number of patients. Different patients are imaged at different times.

The imaging generates an image of the patient. A sequence of images may be generated, such as for viewing change over time and/or for positioning a field of view of the transducer relative to the patient in order to scan the region of interest in the patient.

The settings used for generating one or more of the images are based on user input, default settings, and/or previously output settings from the trained network. The use of the machine-learned network to provide settings of imaging parameters occurs at any time during the examination, such as after acquiring an initial image or later.

In act 17, one of the images is input with or without other information into the machine-learned network. The network has an input feature vector, such as an image, features derived from an image, settings used to acquire the image, patient information, user information, and/or location information.

The information for the current patient, user, and/or location is input to the machine-learned network. The medical ultrasound scanner obtains the patient, user, and/or location information. The information may be obtained from a database, such as the electronic health record of the patient. The information may be obtained from solicitation, such as asking the user to input information to the medical ultrasound scanner as part of the examination of the patient.

The machine-learned network was trained based images for other patients and corresponding settings as negative examples when not stored for the other patients and images for the other patients and corresponding settings as positive examples when stored for the other patients. The training results in the machine-learned network being configured to output values for one or more imaging parameters in response to the input. The input is the image with or without other information (e.g., patient and location). When the network is invoked, the current ultrasound image, imaging parameters, patient information, and region information are collected and fed as input into trained network.

In act 18, the machine-learned network, as implemented by the processor, outputs one or more settings. In response to the input of the image for the current patient and any other information (e.g., the patient, user, and/or location information), one or more values of imaging parameters are output by the machine-learned network.

The output may be a value for a given imaging parameter. A new setting to be used is output. Alternatively, the output is a change in a value from the current value (e.g., adjust by increase of X).

Values for all of the imaging parameters are output as a set. Alternatively, only values being changed are output. In other embodiments, a value or values for a subset of the imaging parameters are output.

This output is converted into imaging action, which results in updating the imaging parameters for generating a next image of the patient. Alternatively, the output is to the user. The user may decide to use the output settings and/or alter the output settings or other settings.

In act 19, the user of the medical ultrasound scanner is notified of the settings. The user may accept, alter, or reject the settings or sub-sets of the settings. The user configures the medical ultrasound scanner to use some or all the settings in the notice. This configuration (e.g., acceptance) may trigger re-imaging of the patient using the current (new) settings. The response to the notification triggers re-imaging.

The user may enable or disable the application of the network. Configuration settings might be available that, when enabled, applies the machine-learned network tuning at all times or specific times during examination.

Figure 4:
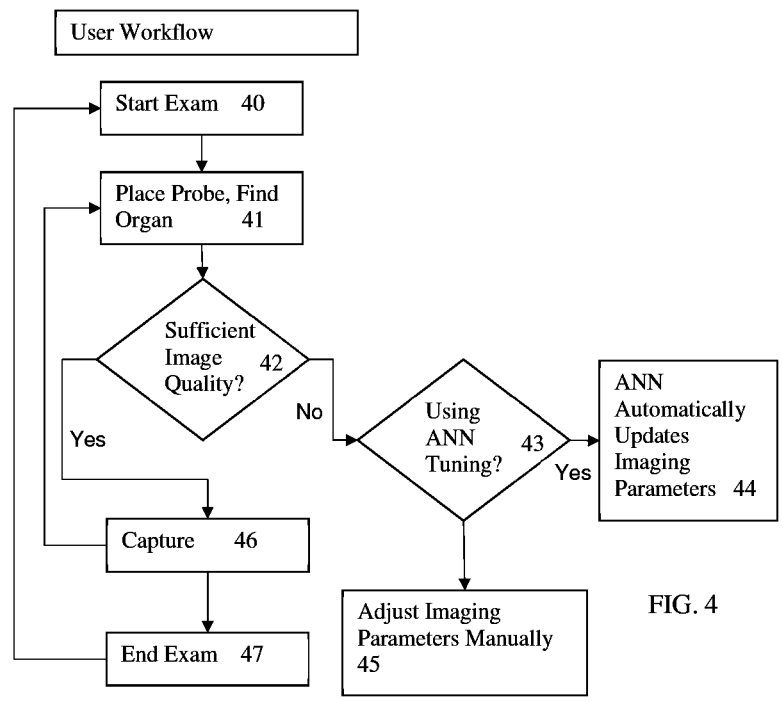
FIG. 4 illustrates an example workflow for using a machine-learned network to provide settings for ultrasound imaging.

FIG. 4 shows one embodiment of a workflow using the machine-learned network in an ultrasound examination of a patient. The machine-learned network runs in the background. When there is a suggestion for imaging parameter update, the user is notified (e.g., a flashing control for the image parameter or parameters).

In act 40, the examination of a patient using an ultrasound scanner is started. Default, user set, or network provided settings are used. In act 41, the patient is imaged to find the region of interest (e.g., organ) using the imaging as configured by the current settings.

Once the region of interest is found, an image of that region of interest may be frozen on the display screen or otherwise viewed by the user. In act 42, the user determines whether the image has sufficient quality for diagnosis for the patient. If so, then the image is captured in act 46. If not, the user or the scanner determines whether to use settings output by the machine-learned network. For example, the image and other information is input to the network and a notification is provided to the user. The user may select in act 43 to use the settings or not. Alternatively, a default selection to use the settings or not is used for act 43. In act 45, the user inputs other settings or adjusts the network-proposed settings. In act 44, the scanner is configured automatically to update the settings with the network output settings. A combination of acts 45 and 44 may be used, such as where the user overrides one setting but not another.

Once new settings are provided, the imaging is performed again and the resulting image checked for quality. Other images may be captured for the patient using the same process (e.g., repeating acts starting at act 41 or act 42). Once the desired images are captured in act 46, the examination ends in act 47.

Returning to FIG. 1, the medical ultrasound scanner re-images the patient using at least one setting from the output of the network in act 20. Other settings may be from output of the network, from manual adjustment of a setting from the network, based on manual entry, or remain the same (e.g., from the default).

Once configured, the scanner images the patient using the new settings. One or more images are generated based on the settings.

In act 21, the image or images generated using configuration based on the machine-learned network output settings are displayed. The images from re-imaging the patient are transmitted to a display device. Acts 17-20 may be repeated until one or more desired images are captured for the patient.

Due to the application of the machine-learned network in the re-imaging of act 20, the image is responsive to the output settings. The image more likely provides diagnostically useful information, avoiding or reducing continuing manual adjustments to find a desired image. Since the patient, location, and/or user information is used by the network in outputting the settings, the image may more likely be a desired image for the current patient, user, and/or region.

The generated image or images for each patient are displayed on a display screen. The physician and/or technician views the image for diagnosis, prognosis, and/or treatment of the patient. The user may save the image, alter the image, transmit the image, discard the image, and/or repeat the image acquisition. This interaction occurs on the medical scanner and/or after storage of the image at another locations (e.g., PACS or electronic health record). The interaction and/or other information generated for the purpose of the patient examination may be used to determine ground truth without expert review for the purpose of creating additional ground truth.

FIG. 3 shows a block diagram of one embodiment of a system for tuned ultrasound imaging. The system implements the method of FIG. 1, 2, or 4, and/or another method. The system is for training with machine learning and/or application of the machine-learned model. For training, the system uses day-to-day patient examination imaging sequences in correspondence with settings to derive ground truth and train based on the derived ground truth. For application, the system inputs an image of a patient being examined and other information to a machine-learned network, which outputs settings used for subsequent imaging during the examination. Other methods or acts may be implemented, such as providing a user interface for approving, displaying notifications, manually altering settings, supervising training, examining a patient, and/or applying a learned model.

The system includes a user input 56, a memory 58, a display 54, a medical scanner 50, and an image processor 52. Additional, different, or fewer components may be provided. For example, the memory 58 is not provided. In another example, a network or network connection is provided, such as for networking with a medical imaging network, electronic medical record, database of user information, memory with location information, or data archival system (e.g., PACS).

The user input 56, memory 58, image processor 52, and/or display 54 are part of the medical scanner 50. Alternatively, the user input 56, memory 58, image processor 52, and/or display 54 are part of a server, workstation, or computer separate from the medical scanner 50. In other embodiments, the image processor 52 and/or memory 58 are part of a remote server for interacting with the medical scanner 50, which includes the remaining components. The user input 56, memory 58, image processor 52, and/or display 54 may be a personal computer, such as desktop or laptop, a workstation, a server, or combinations thereof. In yet other embodiments, the user input 56 and memory 58 are part of a separate computer from the image processor 52.

The medical scanner 50 is a medical diagnostic ultrasound imaging system. The medical scanner 50 includes transmit and receive beamformers, which together with a transducer, scan a patient with ultrasound. The scan is a volume scan, planar scan, linear scan, or scan of a point region. A detector receives beamformed ultrasound data from the scan to detect from the data. A scan converter formats the detected data for display. A memory for color mapping, temporal filter, spatial filter, and/or other components may be included.

The medical scanner 50 is configured by settings for the various components to generate one or more images of a patient during an examination. The settings are for imaging parameters. The configuration is from a memory (e.g., using default values), from a user interface (e.g., using manually entered values), and/or from the image processor 52 (e.g., using values output by a machine-learned network). One or more settings may be changed. The medical ultrasound scanner 50 is configured differently at different times during a same examination (e.g., same appointment or same on-going ultrasound examination with less than 15-minute gap between images). Different settings are used to generate different images in a sequence of images during the examination of a given patient.

The user input 56 is a keyboard, buttons, sliders, knobs, mouse, track-ball, roller ball, touch pad, touch screen, and/or any other user input device or hardware. The user interacts with the system using the user input 56. The patient, treating physician for the patient, radiologist for the patient, and/or technician scanning the patient may interact with the medical scanner 50 and/or the image processor 52 as part of the examination of the patient. These selections, configuration, edits, acceptances, storage, transmission, or other actions for dealing with data about the patient (e.g., images from the medical scanner 50 scan of the patient) may be received by the user input 56, from a memory, and/or from transfer over a network. The actions or results of the actions may be stored and/or transmitted.

The memory 58 is a graphics processing memory, a video random access memory, a random-access memory, system memory, cache memory, hard drive, optical media, magnetic media, flash drive, buffer, combinations thereof, or other now known or later developed memory device for storing training data, images, electronic health record, PACS data, scanner log information, user data, location information, extracted ground truth, settings (e.g., values of imaging parameters), machine-learning architecture, machine-learned network, and/or other information. The memory 58 is part of the medical scanner 50, part of a computer associated with the image processor 52, part of another system, a picture archival memory, or a standalone device. The memory 58 may be formed from a plurality of different memories at the same or different locations. For storing the training data, the memory 58 is a database. Links to patient, user, and/or location data and/or a collection of such data may be stored in the database. The database stores the training data, such as samples from different patients and determined ground truths for the samples.

The memory 58 or other memory is alternatively or additionally a non-transitory computer readable storage medium storing data representing instructions executable by the programmed image processor 52 for learning or applying the machine-learned model. The instructions for implementing the processes, methods, and/or techniques discussed herein are provided on non-transitory computer-readable storage media or memories, such as a cache, buffer, RAM, removable media, hard drive, or other computer readable storage media. Non-transitory computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone, or in combination. Likewise, processing strategies may include multiprocessing, multitasking, parallel processing, and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The image processor 52 is a computer, workstation, server, processor, or other device configured to determine ground truths, apply machine learning, apply a machine-learned model, test a machine-learned model, and/or image a patient. The image processor 52 is configured by software, hardware, and/or firmware. For learning, the image processor 52 is configured by one or more machine learning algorithms to learn to output values of imaging parameters based on an input image and other information. For applying a learned model, the image processor 52 is configured, in part, by a learned matrix or other data (e.g., convolution kernels, pooling connections, and weights) associating input data to output values.

The image processor 52 is configured to determine values of the imaging parameters. The machine-trained network outputs the values in response to input of an image of a patient, the values of the imaging parameters used for that image, and/or patient information for the patient. The network outputs values appropriate for the patient given the patient information and the current image and values. Other inputs may be included, such as a location (e.g., regional designation) of the medical scanner 50 and/or user information for one or more users of the medical scanner 50. The network outputs values appropriate or based on location, patient, and/or user information. The values may be tuned to provide images preferred by the user, in accordance with regional imaging practice, and/or adapted to the patient (e.g., patient's information and/or anatomy being imaged).

For training, the machine-trained network is trained with training data having ground truths inferred from use for other patients of images in scans of the other patients. The regular or on-going use of the scanner 50 for patients is used to establish the ground truth without manual expert entry of the ground truth. Once trained, the image processor 52 is configured to apply the network for other patients.

The image processor 52 is configured to control the ultrasound scanner 50. The user may be notified of recommended values, and the scanner 50 is reconfigured with the new values upon acceptance by the user. Alternatively, the scanner 50 is reconfigured without requiring user notification, or the scanner 50 is reconfigured but does not use the values until confirmation from the user. The values of the imaging parameters as output by the network and/or the values after any modification by the user are used by the scanner 50 to generate an image or sequence of images.

The output of values and use in imaging may be repeated. The user may modify one or more values based on output or without output of the network, and then the scanner 50 generates an image or images. The images desired for diagnosis are captured. Other images may be discarded. The user continues the examination. Due to the network output values, the desired images may be gathered more rapidly or with less manual adjustment by the user. This increases user efficiency and scanner throughput while decreasing patient examination time. The scanner 50 operates in an improved manner to provide more useful images for diagnosis.

The display 54 is a monitor, LCD, projector, plasma display, CRT, printer, or other now known or later developed device for displaying the image or images. The display 54 is configured by a display plane memory or buffer, from which data is read to generate the image on the display screen. The display 54 receives images from the memory 58, image processor 52, or medical scanner 50. The images of the tissue captured by the medical scanner 50 are displayed. Other information may be displayed as well, such as generated graphics, text, or quantities as a virtual overlay.

The image and/or other information may be responsive to a machine-learned model. For example, images from scans of patients are displayed. These images are responsive to output values from the machine-learned model as trained. One or more images may instead be responsive to manually set values and/or default values. Different images are shown throughout an examination to capture a subset of the images for diagnosis, prognosis, and/or treatment of the patient.

When a given patient is examined, the currently existing machine-learned model is applied. The result is patient data or output responsive to the machine-learned model at that time. Since the model may be retrained based on the patient examination provided training data, a different model may be used for later patients. For example, images for different patients are responsive to different versions of the machine-learned model.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for machine learning image optimization with a medical ultrasound scanner, the method comprising:
   imaging, by the medical ultrasound scanner, a patient, the imaging providing a first image where one or more settings are changed after display of the first image and providing a second image resulting from the change in the one or more settings;
   determining, by a computer, ground truth labels for the first image and the second image based at least in part on log data produced by the medical ultrasound scanner during a workflow for examination of the patient, wherein the first image is labeled as a negative example due to the log data indicating that the one or more settings are changed after display of the first image and the second image is labeled as a positive example due to the log data indicating that the second image resulted from the change in the one or more settings;
   machine training, by a machine, a first neural network to output a setting value based on an input image and patient information, wherein the machine training uses the first and second images and the ground truth labels as training data; and
   storing the first neural network as trained.

2. The method of claim 1 further comprising:
   imaging another patient, the imaging providing a third image;
   inputting patient information for the other patient and the third image into the first neural network as trained;
   outputting the setting value in response to the inputting; and
   imaging the other patient using the setting value.

3. The method of claim 1 wherein the imaging for the first image comprises imaging using default values for the settings, and wherein imaging for the second image comprises imaging after a user makes the change to the one or more settings, wherein the ground truth labels are determined based on a sequence in the examination of the patient where the settings are changed from the default values.

4. The method of claim 1 wherein the determining comprises labeling the first image as the negative example for the training based on failure to capture the first image for the patient in a medical record of the patient and labeling the second image as the positive example for the training based on capturing the second image for the patient.

5. The method of claim 1 wherein the machine training comprises machine training with the training data including the first and second images, settings for the first and second images, the settings for the second image including the changed settings, and the patient information.

6. The method of claim 1 wherein the machine training comprises machine training with the patient information comprising clinical characteristics of the patient, patient history, and/or laboratory results.

7. The method of claim 1 wherein the imaging comprises imaging with the workflow for treatment, diagnosis or prognosis of the patient.

8. The method of claim 1 wherein the machine training comprises machine training with the training data including a regional location for the medical ultrasound scanner.

9. The method of claim 1 wherein the imaging comprises imaging by the medical ultrasound scanner operated by a user, and wherein machine training comprises machine training with the training data including information about the user.

10. The method of claim 1 wherein the machine training comprises training an artificial neural network.

* * * * *